United States Patent [19]

Nohira et al.

[11] 4,340,751

[45] Jul. 20, 1982

[54] METHOD OF OPTICAL RESOLUTION OF (±)-2-AMINO-1-BUTANOL AND/OR (±)-MANDELIC ACID

[75] Inventors: Hiroyuki Nohira, 51-5 Ohkubo Ryoke, Urawa, Saitama, Japan; Hiroshi Fujii, Tokyo, Japan; Masami Yajima; Rieko Fujimura, both of Saitama, Japan

[73] Assignee: Hiroyuki Nohira, Urawa, Japan

[21] Appl. No.: 240,789

[22] Filed: Mar. 5, 1981

[30] Foreign Application Priority Data

Mar. 5, 1980 [JP] Japan ................................ 55/26720

[51] Int. Cl.³ ...................... C07B 19/00; C07C 89/04
[52] U.S. Cl. ................................. 562/401; 562/402; 564/303
[58] Field of Search .............. 564/303; 562/401, 402

[56] References Cited

U.S. PATENT DOCUMENTS

| | | | |
|---|---|---|---|
| 3,944,617 | 3/1976 | Singh | 564/303 |
| 4,224,239 | 9/1980 | Tashiro et al. | 562/401 |
| 4,239,912 | 12/1980 | Halmos | 562/401 |
| 4,259,521 | 3/1981 | Kazan et al. | 562/401 |

*Primary Examiner*—Natalie Trousof
*Assistant Examiner*—Vera C. Clarke
*Attorney, Agent, or Firm*—Armstrong, Nikaido, Marmelstein & Kubovcik

[57] ABSTRACT

(±)-2-Amino-1-butanol and/or (±)-mandelic acid are optically resolved with a high resolution efficiency and high optical purities by preferentially crystallizing out one of the pair of less soluble enantiomeric salts (or optical antipodes), namely (+)-2-amino-1-butanol-(+)-mandelic acid salt and (−)-2-amino-1-butanol-(−)-mandelic acid salt.

7 Claims, No Drawings

METHOD OF OPTICAL RESOLUTION OF (±)-2-AMINO-1-BUTANOL AND/OR (±)-MANDELIC ACID

BACKGROUND OF THE INVENTION

1. Field of the Invention

The present invention relates to a method of optical resolution of (±)-2-amino-1-butanol and/or (±)-mandelic acid.

2. State of the Art

2-Amino-1-butanol (hereinafter referred to as "AB") is a compound produced only by chemical synthesis. It is used for synthesis of pharmaceutical and cosmetic products, and as a surface active agent, a vulcanization accelerator, a leather treating agent and in textile treating agents (as an emulsifier for polishing agents and detergents). Particularly, (±)-form of AB is essential as an intermediate compound for synthisis of 2,2'-(ethylene diimino)-di-1-butanol, which is a medical compound having a certain therapeutic effect. (U.S. Pat. No. 3,176,040)

To date, with respect to the optical resolution of (±)-AB, there has been known the methods in which (1) L-tartaric acid is used as the optical resolution agent; Brit. Pat. No. 1,188,185 (1970); J. Am. Chem. Soc. 76 2801 (1954); Chimia 23 399 (1969); and Hung. Pat. No. 157,225 (1970), and, (2) L-glutamic acid is used as optical resolution agent; Span. Pat. No. 357,033 (1970).

These methods utilize optically active acids in natural occurrence and easily available as the resolution agents. Because the solubility, depositability and hygroscopicity of the salts formed by these optically active acids and (±)-AB are unfavorable for the resolution operation under usual conditions, much difficulty is experienced in practice. Moreover, these methods suffer from low resolution efficiency and low optical purities of the products. Thus, the known methods are not advantageous as the commercial processes.

On the other hand, there has been a demand for the optically active mandelic acid (hereinafter referred to as "MA"), because the optically active forms thereof came to be used as a material for medicines, and because they are useful as optical resolution agents. As to obtaining the optically active forms of MA, it has been proposed to use ephedrine or cinchonine. These resolution agents are, however, not easily available in a large quantity. The resolution procedures are complexed and of low efficiency. Further, it is difficult to obtain pure optically active substances.

Japanese Patent Disclosure No. 24849/1979 discloses a method of optical resolution of (±)MA, which comprises reacting (±)MA with (−)AB in a solvent to form diastereomeric salts, separating the precipitated salt from the mother liquor, and decomposing the diastereomeric salts, one of which is the separated crystal and the other remains in the mother liquor, with an acid and an alkali so as to separately recover the optically active acids and (−)AB This method uses optically active (−)AB as the resolution agent as noted above, and therefore, the method requires the preceding step of optical resolution of (±)AB. Unless an inexpensive and convenient method of optical resolution of (±)AB is provided, the disclosed method could not mature in a commercially practicable process.

SUMMARY OF THE INVENTION

The object of the present invention is to overcome the difficulties residing in the above mentioned known methods, and to provide a method of obtaining optically active AB and/or MA with a high resolution efficiency and high optical purities from racemic forms thereof.

The present invention is based on our discovery that the salt of (±)AB and (±)MA is a mixture of a pair of less soluble enantiomeric salts or antipodes, (+)AB-(+)MA salt and (−)AB-(−)MA salt, and that, by preferentially crystallizing out either the (+)AB-(+)MA salt or the (−)AB-(−)MA salt from a supersaturated solution of (±)AB and (±)MA, the optically active AB and/or MA of high optical purities is obtained at a high resolution efficiency.

The present method of optical resolution of (±)AB and/or (±)MA comprises crystallizing out the (+)AB-(+)MA salt or the (−)AB-(−)MA salt from a solution containing (±)AB-(±)MA, separating the crystal salt from the solution, decomposing the separated salts into (+) or (−)AB and (+) or (−)MA, and then, recovering the optically active substances.

In an embodiment of the present method, at least one of (+)AB, (−)AB, (+)MA and (−)MA is added to the above solution containing (±)AB and (±)MA.

In other words, this invention utilizes, for optical resolution of one or both of AB and MA, a mixture of the racemic forms of AB and MA, or a mixture of the racemic forms of AB and MA and an active form of one of AB and MA as the mutually acting resolution agents to form two less soluble enantiomeric salts and to preferentially crystallizing out these salts alternately. Thus, the method enjoys smooth and efficient optical resolution of AB and MA sequentially.

DETAILED DESCRIPTION OF PREFERRED EMBODIMENTS

The present method may be carried out, in the fundamental embodiment, by just adding seed crystal of (+)AB-(+)MA or (−)AB-(−)MA to the supersaturated solution of (±)AB-(±)MA salts so as to use simple alternating preferential crystallization.

Further, it can be carried out by, in case of resolving (±)AB (or (±)MA), using the mixture of an active form of MA (or AB) and the racemic form of MA (or AB).

According to these embodiments, optical resolution of (±)AB (or (±)MA) can be carried out smoothly and efficiently. Furthermore, the (±)MA (or (±)AB) added as the resolution agent is simultaneously optically resolved, and consequently, optically active MA (or AB) in an amount larger than that of the optically active MA (or AB) initially added as the resolution agent can be recovered. This is quite an epoc-making simultaneous mutual optical resolution.

It is preferable to use a specific suitable composition or molar ratio of racemic forms and active forms of AB and MA as mentioned below, because the suitable composition enables smooth and efficient mutual optical resolution, which is the characteristic feature of the present invention, and because the optical purities of the active substances thus obtained are very high.

The preferred embodiment of optical resolution of AB and/or MA comprises preparing the mixed solution of the active forms and racemic forms of AB and MA having the composition (I) or (I') as shown below, crystallizing out a (+)AB-(+)MA salt or (−)AB-(−)MA salt therefrom, and then decomposing these salts to recover (+) or (−)AB and (+) or (−)MA.

| (I). | (+) (or (−)) AB | (a + b) mole |
|---|---|---|
| | (±) AB | (2a + 2b) mole |
| | (+) (or (−)) MA | (2a + b) mole |
| | (±) MA | (a + 2b) mole |
| (I') | (+) (or (−)) MA | (a + b) mole |
| | (±) MA | (2a + 2b) mole |
| | (+) (or (−)) AB | (2a + b) mole |
| | (±) AB | (a + 2b) mole |

Alternatively, the embodiment described below is also preferable because both AB and MA can be mutually and sequentially resolved.

(i) Starting from the mixed solution of active forms of AB and MA and racemic forms of AB and MA having the composition (I) or (I') shown above, (2a+2b) mole of (+)AB-(+)MA salt (or (−)AB-(−)MA salt) is crystallized and separated from the solution;

(ii) the mixture of racemic forms of both AB and MA and the active form of one of AB and MA having the composition (II) or (II') shown below is added to the resulting mother liquor to crystallize (2a+2b) mole of (−)AB-(−)MA salt (or (+)AB-(+)MA salt), which is separated from the solution;

(iii) then, the mixture of the racemic forms of both AB and MA and the active form of one of AB and MA having the composition (III) or (III') shown below is added to the resulting mother liquor to crystallize (2a+2b) mole of (+)AB-(+)MA salt (or (−)AB-(−)MA salt), which is separated from the solution; and (iv) further, the above steps (ii) and (iii) are repeated sequentially, and finally, the separated (+)AB-(+)MA salt and (−)MA-(−)MA salt are decomposed to recover optically active AB and MA.

| (II) | (±) AB | (2a + 2b) mole |
|---|---|---|
| | (−) (or (+)) AB | 2a mole |
| | (±) MA | 2b mole |
| (II') | (±) MA | (2a + 2b) mole |
| | (−) (or (+)) MA | 2a mole |
| | (±) AB | 2b mole |
| (III) | (±) AB | (2a + 2b) mole |
| | (−) (or (+)) AB | 2a mole |
| | (±) MA | 2b mole |
| (III') | (±) MA | (2a + 2b) mole |
| | (−) (or (+)) MA | 2a mole |
| | (±) AB | 2b mole |

The above described preferred embodiment can be ideally conducted by adjusting the quantities of the materials in such a manner that the above noted relation, (I)–(II)–(III) or (I')–(II')–(III') is satisfied. In the formulations, "a" and "b" may be zero to any positive number. If (a:b) equals to (1:0.3 to 3), the mutual optical resolution of AB and MA can efficiently proceed, and therefore, this specific embodiment is particularly advantageous.

In general, however, the mutual optical resolution can be performed without any trouble so long as the materials are used in the amounts ranging from 0.7 to 1.3 times the above mentioned molar relations.

Also, even if the amount of the practically precipitated (+)AB-(+)MA salt or (−)AB-(−)MA salt is more than or less than the theoretical amount, smooth mutual optical resolution could proceed by using the additional materials of the compositions as noted above, or by adjusting the composition of the additional materials so as to form the ideal composition of the solution.

In the practice of the above described sequence of steps (i) through (iv), particularly in preparation of the starting solution having the composition (I) or (I'), it is recommended that the starting solution previously contains additional (±)AB and (±)MA in the amounts giving no appreciable influence on the contemplated optical resolution because certain amounts of (±)AB and (±)MA dissolve in the starting solution and remain in the solution during the operation, thus enabling steady proceeding of the resolution. As may be understood, the ideal amounts of the previously dissolved (±)AB and (±)MA are such that they are equivalent to the maximum soluble amounts of these compounds at the crystallization temperature at which the present method is carried out.

As the medium for preparing the solution containing AB and MA, various solvents such as water, methanol, ethanol, 1-propanol, 2-propanol, acetone and methylethyl ketone can be used solely or in combination. In view of suitable dissolving power and lower price, water, methanol, and 2-propanol are preferable.

For the purpose of crystallizing out (+)AB-(+)MA salt or (−)AB-(−)MA, in case where only (±)AB and (±)MA are dissolved in equal molar quantities, it is necessary to add seeding crystal. In other cases, i.e., dissolved (±)AB and (±)MA are not in equal molar quantities, or at least one of the optical forms of AB and MA is dissolved in the solution, seeding is unnecessary. However, even in the latter cases, it is preferable to use seeding crystal because the active substances of higher purities can be obtained easily, if the seed is used.

Decomposition of the obtained (+)AB-(+)MA salt and/or (−)AB-(−)MA salt into (+) and (−)AB and (+) and (−)MA can be done in accordance with known methods. For example, by acid-decomposing (+)AB-(+)MA salt with dilute hydrochloric acid, (+)MA can be obtained quantitatively, and reacting sodium hydroxide or calcium hydroxide with the remaining mother liquor after concentration thereof, gives free (+)AB, which can be then refined by distillation.

The present invention will now be illustrated with Examples below:

EXAMPLE I 21.7 g (0.244 mole) of (±)AB and 37.1 g (0.244 mole) of (±)MA were dissolved in 100 ml of 99% methanol by being warmed on a water bath under stirring. After completion of the dissolution, the solution was cooled to 6° C., and then, 0.1 g of seed crystals of (+)AB-(+)MA salt ($[\alpha]_{435}^{23} + 139.4°$) was seeded thereto. The solution was allowed to stand at the same temperature over one night, and the precipitated crystals were separated by filtration.

As the product of the first crystallization, 3.5 g of (+)AB-(+)MA salt was obtained. $[\alpha]_{435}^{28} + 114.5°$ (C=1, 99% ethanol)

The resulting mother liquor received addition of 3.0 g of (±)AB-(±)MA salt and 7 ml of 99% methanol, and was warmed on the water bath under stirring. When all the salt was dissolved, the bath was removed to cool the solution to 6° C. Crystal seed, 0.1 g of (−)AB-(−)MA salt was seeded into the solution, and the solution was allowed to stand over one night. The precipitated crystals in the solution were separated by filtration.

The product of the second crystallization was 2.38 g of (−)AB-(−)MA salt. $[\alpha]_{435}^{28} -127.4°$ (C=1, 99% ethanol)

EXAMPLE II 17.8 g (0.200 mole) of (±)AB and 30.4 g (0.200 mole) of (±)MA were dissolved in 50 ml of water by warming on a water bath under stirring. When the dissolution completed, the warming was stopped and the solution was cooled down to 6° C. Seed crystals, 0.1 g of (−)AB-(−)MA salt ($[\alpha]_{435}^{28} -139.7°$) were seeded to the solution, which was then allowed to stand over one night. Then, the precipitated crystals were separated by filtration.

As the product of the first crystallization, 1.42 g of (−)AB-(−)MA salt was obtained. $[\alpha]_{435}^{26} -136.0°$ (C=1, 99% ethanol)

The resulting mother liquor received addition of 1.0 g of (±)AB-(±)MA salt, which dissolved in the liquor under warming and stirring. When complete dissolution was observed, the solution was cooled down to 6° C. Seed crystals, 0.1 g of (+)AB-(+)MA salt ($[\alpha]_{435}^{26} +139.4°$) were seeded to the solution, and the solution was allowed to stand for one night at the same temperature. The precipitated crystals were separated by filtration.

The product of the second crystallization was 0.58 g of (+)AB-(+)MA salt. $[\alpha]_{435}^{28} +135.5°$ (C=1, 99% ethanol).

EXAMPLE III 17.8 g (0.200 mole) of (±)AB and 30.4 g (0.200 mole) of (±)MA were mixed with 60 ml of water, and 2.67 g (0.030 mole) of (+)AB, 5.35 g (0.060 mole) of (±)AB, 7.61 g (0.050 mole) of (+)MA and 6.09 g (0.040 mole) of (±)MA were added to the mixture. All the solid components dissolved in the water by being warmed on a water bath under stirring, and after completion of the dissolution, the warming was stopped to let the solution cool down to the room temperature. Then, 0.1 g of seed crystals, (+)AB-(+)MA salt ($[\alpha]_{435}^{23} +139.4°$) was seeded to the solution, which was subjected to further cooling under continuous stirring. After 4 hours and 30 minutes of crystallization, the liquor was filtered to separate precipitated crystals at 1° C.

As the product of the first crystallization, 12.6 g of (+)AB-(+)MA salt was obtained. $[\alpha]_{435}^{25} +112.2°$ (C=1, 99% ethanol)

The resulting mother liquor received addition of 5.35 g (0.060 mole) of (±)AB, 3.04 g (0.020 mole) of (±)MA, 6.09 g (0.040 mole) of (−)MA and 5 ml of water. The solids dissolved in the water by being warmed on the water bath under stirring, and after completion of the dissolution, the warming was stopped to let the solution cool down to the room temperature. Then, 0.1 g of seed crystals (−)AB-(−)MA salt ($[\alpha]_{435}^{28} -139.7°$) was seeded to the solution, which was further cooled under continuous stirring. After 4 hours of crystallization, the liquor was filtered to separate the precipitated crystals.

The product of the second crystallization was 9.16 g of (−)AB-(−)MA salt. $[\alpha]_{435}^{24} -96.5°$ (C=1, 99% ethanol)

Similar procedures were repeated to give the following results:

| Sequence of Crystallization | Obtained Salt | Yield (g) | $[\alpha]_{435}^{22}$ (C = 1, 99% ethanol) |
| --- | --- | --- | --- |
| 3rd | (+)AB−(+)MA | 11.3 | +121.1° |
| 4th | (−)AB−(−)MA | 13.2 | −119.2° |
| 5th | (+)AB−(+)MA | 15.5 | +112.9° |
| 6th | (−)AB−(−)MA | 10.0 | −124.6° |

11.3 g of (+)AB-(+)MA salt obtained by the above described procedures was recrystallized from the solution in 22 ml of 99% ethanol to give 9.23 g of refined (+)AB-(+)MA salt. $[\alpha]_{435}^{20} +139.0°$ (C=1, 99% ethanol)

4.83 g (0.020 mole) of the refined (+)AB-(+)MA salt was dissolved in 3.6 ml of water under warming, and 4 N-HCl was added to the solution to make it Congo-Red acidic.

Through ether-extraction of this acidic solution and vacuum evaporation of the solvent of the organic phase, 2.96 g of (+)MA crystals were recovered. Recovery from the refined salt: 97.3%, $[\alpha]_{589}^{18.5} +147.4°$ (C=1, 99% ethanol), Optical purity: 95.0%.

Also, through vacuum evaporation of the water phase, 2.28 g of (+)AB hydrochloride was obtained. $[\alpha]_{589}^{23} +13.5°$ (C=5, 99% ethanol)

The (+)AB hydrochloride was dissolved in 2 ml of water, and after addition of 3.2 ml of 6 N-NaOH (0.019 mole) the solution was subjected to gradual removal of water by using a small fine distillation column under the pressure reduced to 30 Torr. 5 ml of methanol was added to the residue to separate NaCl by filtration. Subsequent to removal of the methanol by vacuum evaporation, vacuum distillation of the residue gave 1.37 g of (+)AB. Yield: 77%, b.p.: 79° to 80° C. (12 Torr), $[\alpha]_{589}^{20} +12.5°$ (C=5, 99% ethanol), Optical purity: 98.4%.

Through the similar procedures, 10.7 g of refined (−)AB-(−)MA salt was obtained from 13.2 g of crude (−)AB-(−)MA salt. $[\alpha]_{435}^{22.5} -140.7°$ (C=1, 99% ethanol) From 4.83 g (0.020 mole) of this refined salt, (−)AB-(−)MA salt, the following optical active substances were recovered:

(−)MA 2.94 g Recovery: 96.6% $[\alpha]_{589}^{19} -149.9°$ (C=1, 99% ethanol) Optical purity: 96.5%, and (−)AB 1.39 g Recovery: 78.0% $[\alpha]_{589}^{21.5} -12.2°$ (C=5, 99% ethanol) Optical purity: 96.0%.

EXAMPLE IV 23.8 g (0.266 mole) of (±)AB and 40.6 g (0.266 mole) of (±)MA were mixed with 92 ml of water, and 3,57 g (0.040 mole) of (+)AB, 7.13 g (0.080 mole) of (±)AB, 9.13 g (0.060 mole) of (+)MA and 9.13 g (0.060 mole) of (±)MA were added to the mixture. The solids were dissolved by being warmed on a water bath under stirring. When the dissolution completed, the warming was stopped to let the solution cool down to the room temperature. Seed crystals, 0.1 g of (+)AB-(+)MA salt ($[\alpha]_{435}^{23} +139.4°$) were seeded to the solution, which was further cooled under stirring. After 5 hours and 30 minutes of crystallization, the liquor was filtered to separate the precipitated crystals at 1° C.

As the product of the first crystallization, 18.9 g of (+)AB-(+)MA salt was obtained. $[\alpha]_{435}^{16} +116.5°$ (C=1, 99% ethanol)

The resulting mother liquor received addition of 7.13 g (0.080 mole) of (±)AB, 6.09 g (0.040 mole) of (±)MA and 6.09 g (0.040 mole) of (−)MA. The solids dissolved by being warmed on the water bath under stirring, and after completion of the dissolution, the warming was stopped to let the solution cool down to the room temperature. Seed crystals, 0.1 g of (−)AB-(−)MA salt were seeded to the solution, which was further cooled under stirring. After 6 hours and 30 minutes, the precipitated crystals were separated by filtration at 1° C.

The product of the second crystallization was 14.7 g of (−)AB-(−)MA salt. $[\alpha]_{435}^{16} -118.8°$ (C=1, 99% ethanol)

The following results were obtained by repeating the similar procedures:

| Sequence of Crystallization | Obtained Salt | Yield (g) | $[\alpha]_{435}^{20}$ (C = 1, 99% ethanol) |
|---|---|---|---|
| 3rd | (+)AB−(+)MA | 16.2 | +116.7 |
| 4th | (−)AB−(−)MA | 15.6 | −110.2° |
| 5th | (+)AB−(+)MA | 16.5 | +121.1° |
| 6th | (−)AB−(−)MA | 18.0 | −114.2° |

EXAMPLE V 11.9 g (0.133 mole) of (±)AB and 20.2 g (0.133 mole) of (±)MA were mixed with 32 ml of water, and 2.67 g (0.030 mole) of (+)AB, 2.67 g (0.030 mole) of (±)AB, 3.04 g (0.020 mole) of (+)MA and 6.08 g (0.040 mole) of (±)MA were added to the mixture.

The solids were dissolved by being warmed on a water bath under stirring, and after completion of the dissolution, the warming was stopped to let the solution cool down to the room temperature. Seed crystal, 0.1 of (+)AB-(+)MA salt ($[\alpha]_{435}^{23} +139.4°$) was seeded to the solution, which was further cooled under stirring. After 5 hours of crystallization, the precipitated crystal was separated by filtration.

As the product of the first crystallization, 9.01 g of (+)AB-(+)MA salt was obtained. $[\alpha]_{435}^{20} +110.6°$ (C=1, 99% ethanol)

6.09 g (0.040 mole) of (±)MA, 1.79 g (0.020 mole) of (±)AB and 1.78 g (0.020 mole) of (−)AB were added to the resulting mother liquor. The admixture was warmed on the water bath and stirred to dissolve the solids. When the dissolution completed, the warming was stopped to let the solution cool down to the room temperature. Subsequent to the seeding by addition of crystals of 0.1 g of (−)AB-(−)MA salt, the solution was further cooled and stirred for crystallization. The liquor was filtered when 5 hours elapsed, at 10° C., to separate the precipitated crystals The product of the second crystallization was 7.63 g of (−)AB-(−)MA salt. $[\alpha]_{435}^{20.5} -110.7°$ (C=1, 99% ethanol)

By repeating similar procedures, the following salts were obtained:

| Sequence of Crystallization | Obtained Salt | Yield (g) | $[\alpha]_{435}$ |
|---|---|---|---|
| 3rd | (+)AB−(+)MA | 7.49 | +113.4 |
| 4th | (−)AB−(−)MA | 7.82 | −115.1 |

We claim:
1. A method of optical resolution of at least one of (±)-2-amino-1-butanol (AB) and (±)-mandelic acid (MA), which method comprises the steps of:

(i) crystallizing out, from a solution containing (±)AB and (±)MA, one of the pair of (+)AB-(+)MA salt and (−)AB-(−)MA salt, both of which are contained in said solution and which are enantiomeric salts;
(ii) separating the crystallized salt from the liquid;
(iii) decomposing the enantiomeric salt into optically active AB and MA; and
(iv) recovering the optically active substances.

2. A method of optical resolution according to claim 1, wherein the solution medium is selected from the group consisting of water, methanol and 2-propanol.

3. A method of optical resolution according to claim 1, wherein at least one of (+)AB, (−)AB, (+)MA and (−)MA coexists in the solution containing (±)AB and (±)MA.

4. A method of optical resolution according to claim 1, wherein the resolution starts from a mixture solution of AB and MA of the composition selected from the following (I) and (I'):

| (I) | (+) (or (−)) AB | (a + b) mole |
|---|---|---|
| | (±) AB | (2a + 2b) mole |
| | (±) MA | (2a + b) mole |
| | (±) MA | (a + 2b) mole |
| (I') | (+) (or (−)) MA | (a + b) mole |
| | (±) MA | (2a + 2b) mole |
| | (+) (or (−)) AB | (2a + b) mole |
| | (±) AB | (a + 2b) mole. |

5. A method of optical resolution according to claim 4, wherein the molar amounts of the components in the mixture solution are within the range of 0.7 to 1.3 times of the value given by the formulation (I) or (I').

6. A method of optical resolution according to claim 4, which comprises the steps of:
(i) starting from the mixture solution of the composition selected from the above noted (I) and (I'), crystallizing out (2a+2b) mole of the enantiomeric salt, (+)AB-(−)MA or (−)AB-(−)MA, followed by separation of the crystal from the liquid;
(ii) adding to the resulting mother liquor the mixture of racemic forms of both AB and MA and an optically active form of one of AB and MA of the composition selected from (II) and (II') below:

| (II) | (+) AB | (2a + 2b) mole |
|---|---|---|
| | (−) (or (+)) AB | 2a mole |
| | (±) MA | 2b mole |
| (II') | (±) MA | (2a + 2b) mole |
| | (−) (or (+)) MA | 2a mole |
| | (±) AB | 2b mole | so as to crystallize out (2a+2b) mole of the enantiomeric salt of (−)AB-(−)MA or (+)AB-(+)MA, followed by separation of the crystal from the liquid;
(iii) adding to the resulting secondary mother liquor the racemic forms of both AB and MA and an optically active form of one of AB and MA of the composition selected from (III) or (III') below:

| (III) | (±) AB | (2a + 2b) mole |
|---|---|---|
| | (±) (or (−)) AB | 2a mole |
| | (±) MA | 2b mole |
| (III') | (±) MA | (2a + 2b) mole |
| | (+) (or (−)) MA | 2a mole |

| -continued | |
|---|---|
| (±) AB | 2b mole | so as to crystallize out (2a+2b) mole of the enantiomeric salt of (+)AB-(+)MA or (−)AB-(−)MA, followed by separation of the crystal from the liquid; and, (iv) repeating the above steps (ii) and (iii) sequentially, and finally, decomposing the obtained enantiomeric salts to optically active AB and MA, and recovering them.

7. A method of optical resolution according to claim 6, wherein the molar amounts of the components in the mixture are within the range of 0.7 to 1.3 times of the value given by the formulations (I) or (I′), (II) or (II′), and (III) or (III′).

* * * * *

UNITED STATES PATENT AND TRADEMARK OFFICE
CERTIFICATE OF CORRECTION

PATENT NO. : 4,340,751
DATED : July 20, 1982
INVENTOR(S) : HIROYUKI NOHIRA ET AL It is certified that error appears in the above-identified patent and that said Letters Patent is hereby corrected as shown below:

Column 3, line 36: change "(-)MA-(-)MA" to --(-)AB-(-)MA-- .
Column 3, approximately line 40 (first line under "(II)"): change "(-)(or(+))AB" to --(-)(or(+))MA--.
Column 3, approximately line 42, (first line under "(II')"): change "(-)(or(+))MA" to --(-)(or(+))AB--.
Column 3, approximately line 45 (first line under "(III)"): change "(-)(or (+))AB" to --(+)(or(-))MA--.
Column 3, approximately line 48 (first line under "(III')"): change "(-)(or (+))MA" to --(+)(or(-))AB--.
Column 4, line 25, after "MA" insert --salt--.

Column 7, line 42: change "1.79 g" to --1.78 g--.
Column 8, line 25 (second line under "(I)"): change "(+)MA" to --(+)(or (-))MA--.
Colum 8, line 40: change "(+)AB-(-)MA" to --(+)AB-(+)MA--.
Column 8, approximately line 48 (adjacent "(II)"): change "(+)AB" to --(±)AB--.
Column 8, approximately line 49 (first line under "(II)"): change "(-)(or(+))AB" to --(-)(or(+))MA--.
Column 8, approximately line 52, (first line under "(II')"): change "(-)(or(+))MA" to --(-)(or(+))AB--.

UNITED STATES PATENT AND TRADEMARK OFFICE
CERTIFICATE OF CORRECTION

PATENT NO. : 4,340,751

DATED : July 20, 1982

INVENTOR(S) : HIROYUKI NOHIRA ET AL

It is certified that error appears in the above-identified patent and that said Letters Patent is hereby corrected as shown below:

Column 8, approximately line 65 (first line under "(III)"): change "(±)(or(-))MA" to --(+)(or(-))AB--.
Column 8, last line, change "MA" to --AB--.

Signed and Sealed this

Eighth Day of October 1985

[SEAL]

Attest:

DONALD J. QUIGG

Attesting Officer

Commissioner of Patents and Trademarks—Designate